United States Patent
Richey, II et al.

[11] Patent Number: 5,988,165
[45] Date of Patent: Nov. 23, 1999

[54] APPARATUS AND METHOD FOR FORMING OXYGEN-ENRICHED GAS AND COMPRESSION THEREOF FOR HIGH-PRESSURE MOBILE STORAGE UTILIZATION

[75] Inventors: Joseph B. Richey, II, Chagrin Falls; Gerold G. Goertzen, Brunswick, both of Ohio

[73] Assignee: Invacare Corporation, Elyria, Ohio

[21] Appl. No.: 08/942,063

[22] Filed: Oct. 1, 1997

[51] Int. Cl.⁶ .............. A62B 7/10; A62B 19/00; A62B 23/02

[52] U.S. Cl. .............. 128/205.12; 128/205.11; 128/205.27; 128/204.22

[58] Field of Search .............. 128/205.12, 205.18, 128/204.18, 207.26, 200.24, 205.11, 205.27, 204.22, 204.24, 204.25, 204.21; 141/2, 3, 4, 18, 21; 95/100; 96/130; 417/27, 244, 243

[56] References Cited

U.S. PATENT DOCUMENTS

| | | |
|---|---|---|
| 2,944,627 | 7/1960 | Skarstrom . |
| 3,313,091 | 4/1967 | Berlin . |
| 3,898,047 | 8/1975 | Cramer .............. 128/202.26 |
| 4,013,429 | 3/1977 | Sircar et al. .............. 95/130 |
| 4,194,890 | 3/1980 | McCombs et al. . |
| 4,222,750 | 9/1980 | Gauthier et al. . |
| 4,331,455 | 5/1982 | Sato .............. 128/202.26 |
| 4,428,372 | 1/1984 | Beysel et al. .............. 128/202.26 |
| 4,449,990 | 5/1984 | Tedford, Jr. .............. 95/130 |
| 4,552,571 | 11/1985 | Dechene . |
| 4,627,860 | 12/1986 | Rowland .............. 95/130 |
| 4,636,226 | 1/1987 | Canfora .............. 96/130 |
| 4,673,415 | 6/1987 | Stanford .............. 96/130 |
| 4,706,664 | 11/1987 | Snook et al. .............. 128/204.21 |
| 4,765,804 | 8/1988 | Lloyd-Williams et al. .............. 96/130 |
| 4,844,059 | 7/1989 | Koch . |
| 4,867,766 | 9/1989 | Campbell et al. .............. 96/130 |
| 4,869,733 | 9/1989 | Stanford .............. 96/130 |
| 4,905,685 | 3/1990 | Olsson et al. .............. 128/203.12 |
| 4,991,616 | 2/1991 | Fabregat . |
| 5,071,453 | 12/1991 | Hradek et al. . |
| 5,144,945 | 9/1992 | Nishino et al. .............. 128/205.12 |
| 5,195,874 | 3/1993 | Odagiri .............. 417/27 |
| 5,199,423 | 4/1993 | Harral et al. . |
| 5,237,987 | 8/1993 | Anderson et al. .............. 128/204.18 |
| 5,354,361 | 10/1994 | Coffield . |
| 5,474,595 | 12/1995 | McCombs .............. 95/130 |
| 5,584,669 | 12/1996 | Becker . |

FOREIGN PATENT DOCUMENTS

| | | |
|---|---|---|
| 860 647 | 8/1998 | European Pat. Off. . |
| 374 540 | 6/1932 | United Kingdom . |

*Primary Examiner*—John G. Weiss
*Assistant Examiner*—Joseph F. Weiss, Jr
*Attorney, Agent, or Firm*—Hudak & Shunk Co.

[57] ABSTRACT

An oxygen concentrator is utilized in combination with a compressor to provide a highly enriched and compressed oxygen gas in a mobile container such as a gas cylinder. The combination and method of production provides for the facile preparation of an enriched source of oxygen for use by an ambulatory or wheelchair-confined patient. The oxygen concentrator utilizes two or more molecular sieves to provide a breathable gas of from approximately 80 to about 98 percent oxygen from atmospheric air. The oxygen-enriched gas is stored in a concentrator product tank and can be prioritized so as to supply a patient with a proper amount and concentration of oxygen and secondarily to supply any surplus or excess enriched oxygen to a compressor. The compressor utilizes multiple stages to produce the highly compressed oxygen-enriched gas and utilizes a two-part piston at low rpm to enhance low wear and low noise.

26 Claims, 6 Drawing Sheets

APPARATUS AND METHOD FOR FORMING OXYGEN-ENRICHED GAS AND COMPRESSION THEREOF FOR HIGH-PRESSURE MOBILE STORAGE UTILIZATION

FIELD OF INVENTION

The present invention relates to an apparatus and process for producing enriched oxygen which is subsequently collected under high pressure in a portable container for ambulatory patient use and to permit facile patient mobility.

BACKGROUND OF THE INVENTION

Heretofore, oxygen concentrators have been utilized to supply patients with a gas having a high oxygen concentration for extended periods of time. Oxygen concentrators typically produce a breathable gas containing from about 80 percent to about 96 percent oxygen from atmospheric air and thus have been widely utilized in the home health care field.

U.S. Pat. No. 4,627,860, to Rowland, relates to a microprocessor and cooperating means for monitoring or sensing functions and performance of various components of the concentrator. A test apparatus having means for selecting any of the functions monitored by the microprocessor is connected to the concentrator and displays the selected monitored functions for diagnosing performance levels and component problems or failures.

U.S. Pat. No. 5,071,453, to Hradek et al. relates to an oxygen concentrator which is intended for aircraft use. A booster compressor is used to increase the pressure of the product gas from the concentrator in order to increase the amount of the gas which can be stored in a plenum. The booster includes two moving pistons which are rigidly linked together and a series of check valves which control the flow of gases through the compressor. One of the pistons is driven by air from the rotary valve in the concentrator, and the other piston compresses the product gas for delivery to the plenum. A small sample of concentrator product gas is monitored by an oxygen sensor for oxygen concentration. Once the oxygen concentration has reached an acceptable level, the booster compressor fills the plenum with product gas. Thereafter, if the oxygen concentration of product gas delivered to the crew from the concentrator falls below the concentration which is required at a particular altitude, the product gas stored in the plenum is delivered to the crew. The oxygen sensor monitors the concentrator output product gas to the breathing regulator when the stored plenum gas is not being used.

U.S. Pat. No. 5,354,361, to Coffield, relates to a pressure-swing adsorber system including a pneumatically driven booster compressor to increase the pressure of the output product gas. A pair of inlet valves controls feed air flow to the sieve beds and the drive cylinder of the booster compressor and are cycled so that one valve opens to pressurize one sieve bed before the other valve closes to allow the other sieve bed to vent to atmosphere. During the time that both valves are open, the pressure in the two sieve beds and on opposite sides of the drive cylinder equalize and a portion of the gas in the pressurized sieve bed and drive cylinder side is captured rather than being vented to ambient. System efficiency is increased by selecting whether captured gas from the last pressurized sieve bed or drive cylinder side reaches the next to be pressurized sieve bed first.

SUMMARY OF THE INVENTION

It is an aspect of the present invention to provide a method and apparatus for storing high-pressure, high-purity oxygen in a pressure vessel for use in the home health care or related fields as for ambulatory patients, persons confined to wheelchairs, and those who are bedridden.

In accordance with the invention there is provided a method and apparatus for producing from air an oxygen-enriched gas and initially storing the same in a concentrator product tank. Desirably but secondarily, at least a portion of the oxygen-enriched gas is fed by different methods to a compressor buffer tank where it is stored. After reaching a predetermined pressure, the gas is fed to a compressor where it is compressed to a high pressure and stored in a mobile or portable high-pressure container. This eliminates the requirement of an oxygen concentrator which contains a first compressor and requires connection to an electrical outlet. A patient can thus have increased mobility through use of the portable, high-pressure oxygen container.

It is a further aspect of the invention to provide electrical circuitry to assure prioritization of the flow rate and concentration of the enriched gas to a patient. The excess gas, when available, is simultaneously delivered to an independent, multi-stage compressor.

In accordance with another aspect of the invention there is provided a home health care oxygen concentrator for physically separating molecules of oxygen from air with oxygen in a subsequent operation being fed to a high-pressure vessel. The concentrator comprises one or more molecular sieve beds containing a physical separation material, a first (i.e., feed stock) compressor to provide a feed source of compressed air, control means which regulate the product gas flow through the beds to a concentrator product tank, a second enriched-gas storage tank (i.e., a buffer tank), and a second compressor, e.g., multi-stage, which is not operated by the first compressor but operates independently thereof and enables the oxygen-enriched gas to be compressed and fed to a high-pressure vessel or container. The second compressor has a two-part piston assembly which results in low wear.

DETAILED DESCRIPTION OF THE PREFERRED EMBODIMENT

While a preferred embodiment of the invention is described hereinbelow, it is to be understood that the various aspects and parameters of the present invention can vary and be different such as the pressure and purity of the oxygen-enriched gas exiting from a concentration product tank, the pressure at which the enriched gas is fed to the patient and its flow rate, the pressure maintained in a buffer tank, the pressure at which the compressor initially draws enriched gas from the buffer tank, the buffer tank pressure at which the compressor shuts off, and the like. Moreover, while reference is made to a particular oxygen concentrator as set forth immediately below, generally any type of oxygen concentrator can be utilized which yields a source of enriched oxygen containing anywhere from about 50 percent oxygen up to about 99 percent by volume.

Figure 1:
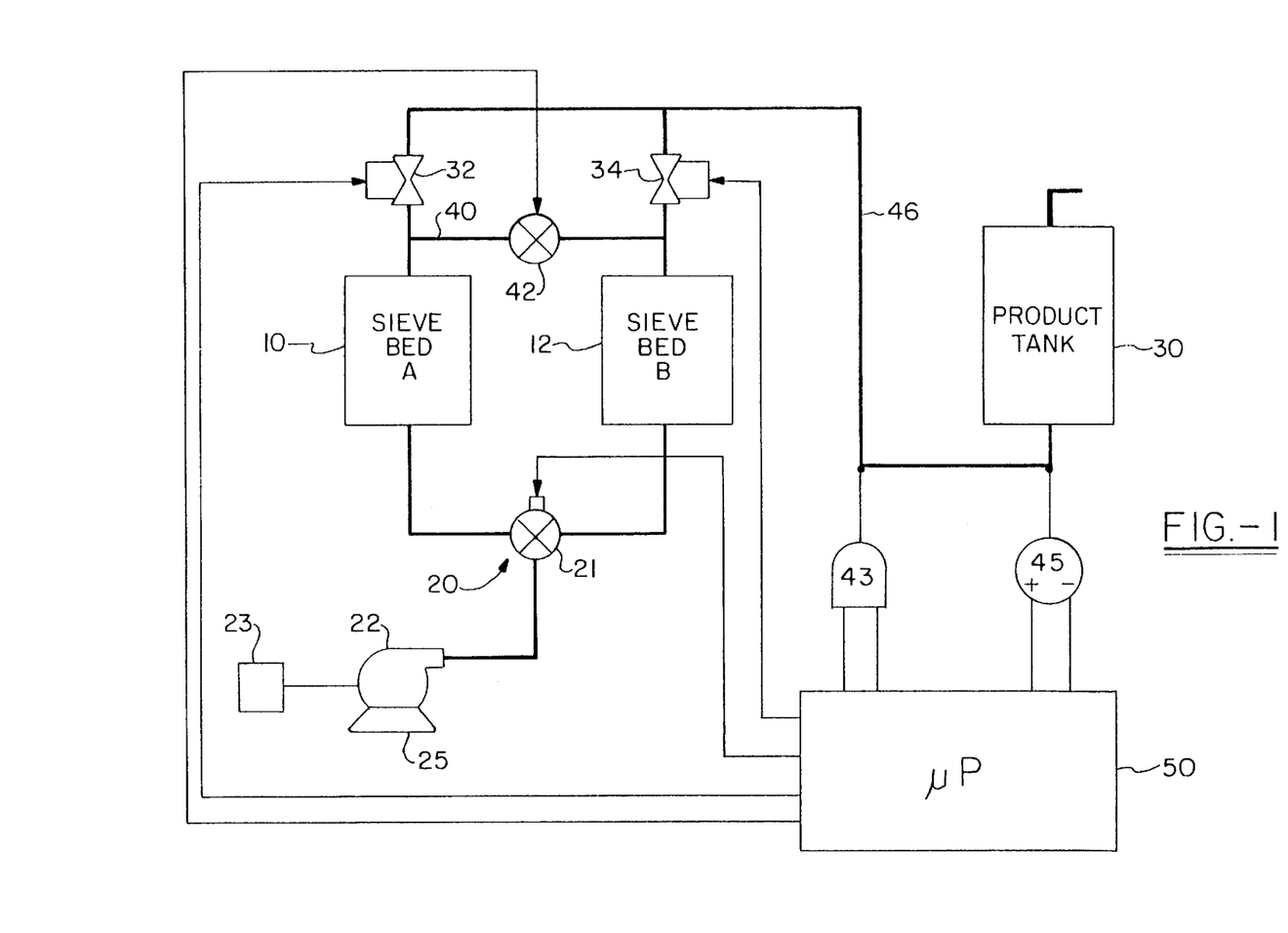
FIG. 1 is a block diagram of an oxygen concentrator for separating oxygen from a gaseous mixture such as air.

With reference to FIG. 1, the apparatus includes one or more, and preferably two beds 10 and 12 which contain a physical separation medium or material. The separation material selectively adsorbs one or more adsorbable components as from air and passes one or more nonadsorbable components of such a gaseous mixture. The physical separation material can be a molecular sieve with pores of uniform size and essentially the same molecular dimensions. These pores selectively adsorb molecules in accordance with molecular shape, polarity, degree of saturation, and the like. In the preferred embodiment, the physical separation medium is an aluminasilicate composition with 4 to 5 Å (Angstrom) pores. More specifically, the molecular sieve is a sodium or calcium form of aluminasilicate, such as type 5A zeolite. Alternately, the aluminasilicate may have a higher silicon-to-aluminum ratio, larger pores, and an affinity for polar molecules, e.g., type 13× zeolite. The zeolite adsorbs nitrogen, carbon monoxide, carbon dioxide, water vapor, and other significant components of air.

A cross-over valving means 20, which preferably includes a four-way valve 21, selectively and cyclically connects the inlet end of two beds, one at a time, during a production phase with a source of the gas mixture, e.g., air under pressure supplied from a first compressor 22 (i.e., the feed compressor), while the other bed is vented to atmosphere during a purge phase. Specific to the preferred embodiment, the cross-over valving means selectively connects one of the beds in fluid communication with an air pump or compressor 22 which supplies air from about 15 to about 21 psi. As used herein, "fluid communication" refers to means allowing flow of the appropriate gases. Of course, vacuum can also be used during the purge phase with the present invention to enhance evacuation. Compressor 22, which receives air from inlet 23, is connected to a first drive motor 25, in the preferred embodiment about a ¼-horsepower electric motor. A solenoid (not shown) or other cross-over valve actuating means selectively causes the cross-over valving means to move alternately between first and second positions. In the first position, the first bed 10 is connected with compressor 22 to cause nitrogen adsorption and oxygen enrichment in the product gas, and the second bed 12 is vented to atmosphere to allow evacuation. In the second position, the first bed is vented to atmosphere to allow evacuation and the second bed is connected with the air compressor to cause nitrogen adsorption. The invention is described with specific reference to a pressure-swing control. However, it is equally applicable to other methods of sequencing the gas flow through the sieve beds such as a timing-based system.

The composition of the gas in the voids of the zeolite varies from substantially pure primary-product gas at the outlet end, to the ambient gaseous mixture composition at the inlet end. As the gas mixture is introduced through a bed inlet to an adsorbed, gas-free or regenerated bed, an adsorption zone of finite, relatively large size is formed. This adsorption zone is a region of the bed in which the full capacity of the adsorbent to hold the adsorbable components has not been reached. This adsorption zone moves from the bed inlet toward a bed outlet with a velocity significantly less than the superficial gas velocity in the bed. When the adsorption zone reaches the outlet end of the bed, adsorbable components begin to flow through the bed outlet into the nonadsorbable primary product stream. This time is hereinafter referred to as the "breakthrough." For a given gaseous composition, the breakthrough is defined by the size and configuration of the bed container as well as the packing configuration of the molecular sieve and the flow rate and bed gas pressure. The configuration of the bed is generally cylindrical and the output volume rate can vary from about 0.1 to 6 liters per minute. The breakthrough is the time required for the diffusion reaction as the nitrogen saturates and is weakly bonded to the sieve bed. When breakthrough occurs, primary product-enriched bed gas in the zeolite voids varies from a higher primary product gas concentration at the bed outlet to a lower concentration at the bed inlet. In the preferred embodiment, the primary product-enriched bed gas is about 80 percent primary product at breakthrough. While adsorption is occurring in one bed, the adsorbable components adsorbed by the separation medium of the other bed are purged from the other bed because of the drop in pressure due to atmospheric venting and because of exposure to relatively pure product gas from the first tank.

The first bed 10 is connected with a reservoir or product tank 30 by way of a first check valve 32 or other unidirectional valving means. The first check valve 32 permits the primary product gas from the first bed 10 to flow into the reservoir or product tank 30 via line 46 when the product gas pressure in the first bed 10 exceeds the pressure of product gas in the reservoir or product tank 30. The first check valve prohibits the product gas from flowing from the reservoir or product tank 30 when the pressure in the first bed 10 is lower than the reservoir or product tank. More specific to the preferred embodiment, the check valve imposes a 1.5 psi bias such that flow is only permitted when the pressure in the first bed exceeds the pressure in the reservoir or product tank by 1.5 psi. The second bed 12 is connected with the reservoir or product tank 30 by way of a second check valve 34 or other unidirectional valving means. The second check valve 34 again provides for unidirectional flow of the primary product gas from the second bed 12 to the reservoir or product tank 30.

A pressure equalization flow path 40 extends between outlets of the first and second beds. A concentration equalization valve 42 is either open or closed to selectively permit or prevent gas flow through the flow path between the first and second beds. A control means 50 cyclically causes the cross-over valve actuating means (i.e., two solenoids) and the concentration equalization valve 42 to be operated. The control means periodically and cyclically enables a concentration equalization valve actuator which is also a solenoid.

Oxygen sensor 43 registers the oxygen concentration of the product gas and can be located in the product tank 30. The sensor 43 communicates a sensed value to the microprocessor (i.e., control means). Similarly, a pressure sensor 45 registers the pressure in the product tank and communicates the same to the microprocessor.

The control means causes the cross-over valving means 20 to alternate between its first and second positions for the appropriate period during each cycle segment. A cycle segment can be either the product gas generation cycle or the purge cycle. The cycle duration is selected such that each bed is connected with the source of air for a period of time which is equal to or less than the breakthrough time. The mechanism which triggers the cross-over valving can be based on the pressure, such as a pressure set point or set point range, in the bleed line from the product tank as is used in a pressure-based control cycle, or it can be based strictly on a residence time from the product-producing bed, such as in a timing cycle-based control cycle. In accordance with another embodiment of the invention, the control cycle can utilize variable pressure in order to achieve a residence time within a defined range based upon a projected breakthrough time. In the preferred embodiment, the beds are 3.5 inches in diameter, 15 inches in length, and each contains 6.5 pounds of 5A zeolite.

The gas mixture is supplied at up to 21 psi of pressure to the first bed. Concurrently, the second bed (i.e., a "used" bed) is vented to atmosphere to cause purging of the nitrogen-enriched molecular sieves. Before the breakthrough time, the concentration equalization valve is opened allowing primary product-enriched gas from the first bed to flow into the evacuated second bed. During the concentration equalization period, one bed is evacuated and the other has just reached the pressure set point which drives flow between the beds. The flow is of high oxygen content so that the first product to pass into the product tank via line 46 is essentially product gas produced by the oxygen beds. The second bed pressure is product-enriched gas to purge the sieve bed. Before the primary product-enriched gas from the first bed is evacuated through the second bed, the cross-over valving means 20 is actuated to reverse its position. Actuating the cross-over valving means discontinues supplying of the gaseous mixture to the first bed and commences evacuating it and concurrently discontinues evacuating the second bed and commences supplying it with the gaseous mixture.

Subsequent to the actuation of the cross-over valving means, the concentration equalization valve 42 remains open to continue allowing a purge supply of product-enriched gas to flow into the second bed. This equalizes the concentration of gas which is supplied to the product tank since the cycling is sequenced so that the product gas proceeds from the breakthrough zone to flow into the product tank. Subsequently, the concentration equalization valve closes and terminates the flow of primary-product gas between the beds. In the second segment of the cycle, the pressure in the second bed increases approaching the gas mixture source pressure. Concurrently, the pressure in the first bed decreases approaching atmospheric pressure. Before the secondary product molecules have traversed the second bed, the concentration equalization valve 42 is opened allowing the primary product-enriched gas in the zeolite voids of the second bed to flow to the first bed. While the primary product-enriched gas is flowing to the first bed, the cross-over valving means is actuated. Actuating the cross-over valving means discontinues the evacuation of the first bed and commences supplying the gaseous mixture and concurrently discontinues supplying the gaseous mixture to the second bed and commences evacuating it. Subsequent to actuating the cross-over valving means, the concentration equalization valve is closed terminating the pressure equalizing flow of the primary product-enriched gas between the beds. The steps are cyclically repeated to provide continuing fractionating of the primary product gas from the mixture.

Referring again to FIG. 1, in a preferred embodiment the reservoir or product tank 30 maintains a reservoir of oxygen at a minimum pressure of about 14 psi. The oxygen-enriched gas contains from about 50 to about 99 percent, desirably from about 70 to about 98 percent, and preferably from about 84 to about 96 percent by volume of oxygen. In accordance with conventional procedures, product tank 30 can be connected to a pressure regulator (not shown) for controlling the pressure of the oxygen to a patient. Typically a pressure of 5 psi is utilized. A flow meter (also not shown in FIG. 1) can be utilized to limit the flow rate to the patient such as from 0.1 to about 6 liters per minute with a flow rate of about 3 liters per minute often being utilized. If desired, a humidifier (not shown) can add moisture to the oxygen-enriched gas. The gas is delivered to the patient via tubing and breathing apparatus which can be inserted into the patient's nostrils.

In accordance with other concepts of the present invention, oxygen-enriched gas from an oxygen concentrator such as that described hereinabove can be fed in any variety of methods to a compressor where it is compressed to very high pressure and stored in a portable or mobile container such as a gas cylinder.

Figure 2:
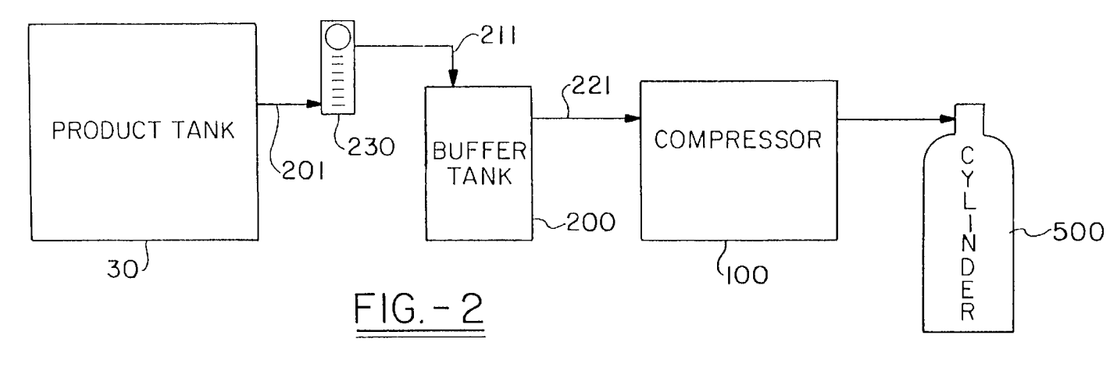
FIG. 2 is a block diagram of an apparatus and process in accordance with the present invention for compressing oxygen-enriched air and feeding it to a portable container.

In the embodiment of FIG. 2, all of the oxygen-enriched gas is fed to a compressor. A concentrator (not shown but such as described hereinabove) has an oxygen-enriched product tank 30 wherein the pressure can vary as from about 14 to about 21 psi. The oxygen-enriched gas therein is fed via line 201 to a flow meter 230 at the pressure of the concentrator tank, that is from about 14 to about 21 psi. Flow meter 230 controls the flow rate of the oxygen-enriched gas which is fed via line 211 to buffer tank 200 wherein the gas pressure therein can also range from about 14 to about 21 psi. Via line 221, the predominantly oxygen gas is fed to compressor 100. Compressor 100, in a manner described below, compresses the oxygen-enriched gas to a pressure of about 2,250 psi and stores it within a mobile or portable cylinder 500. Depending upon the withdrawal rate of the oxygen-enriched gas by the compressor, the feed pressure thereto can range from 21 psi down to a predetermined cut-off pressure such as about 5 or 7 psi whereupon the compressor is automatically shut off by a pressure sensor switch.

Figure 3:
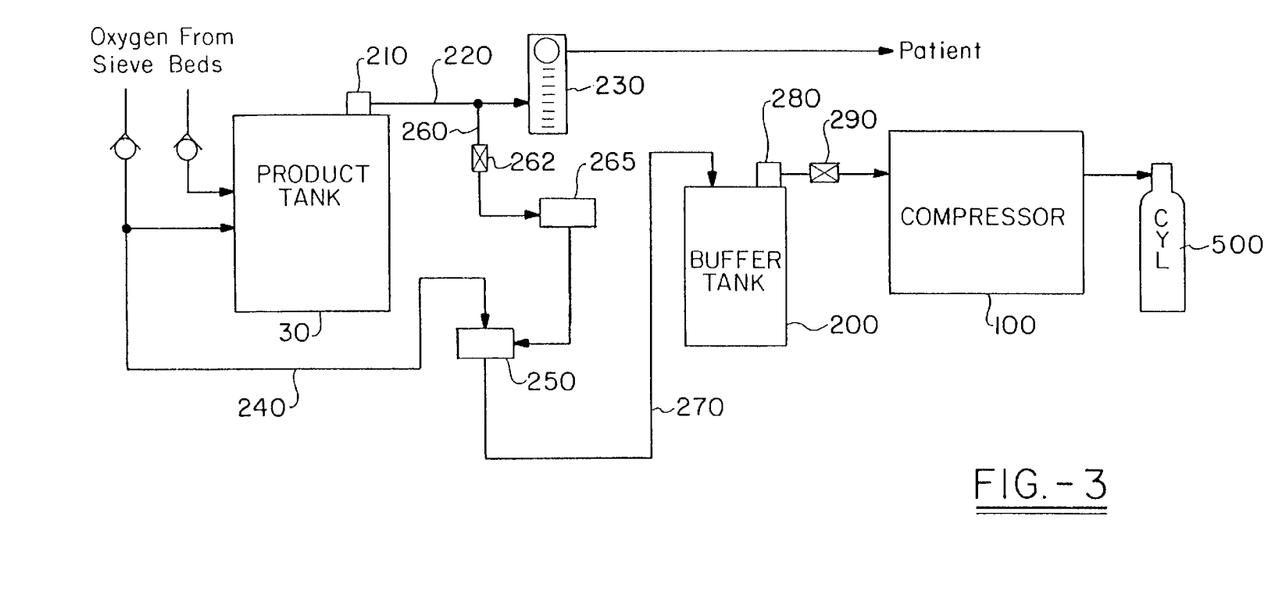
FIG. 3 is a block diagram of the apparatus and process of the present invention for feeding a portion of enriched gas at a controlled rate to a patient and another portion of the enriched gas to a compressor for high-pressure storage in a portable container.
Figure 4:
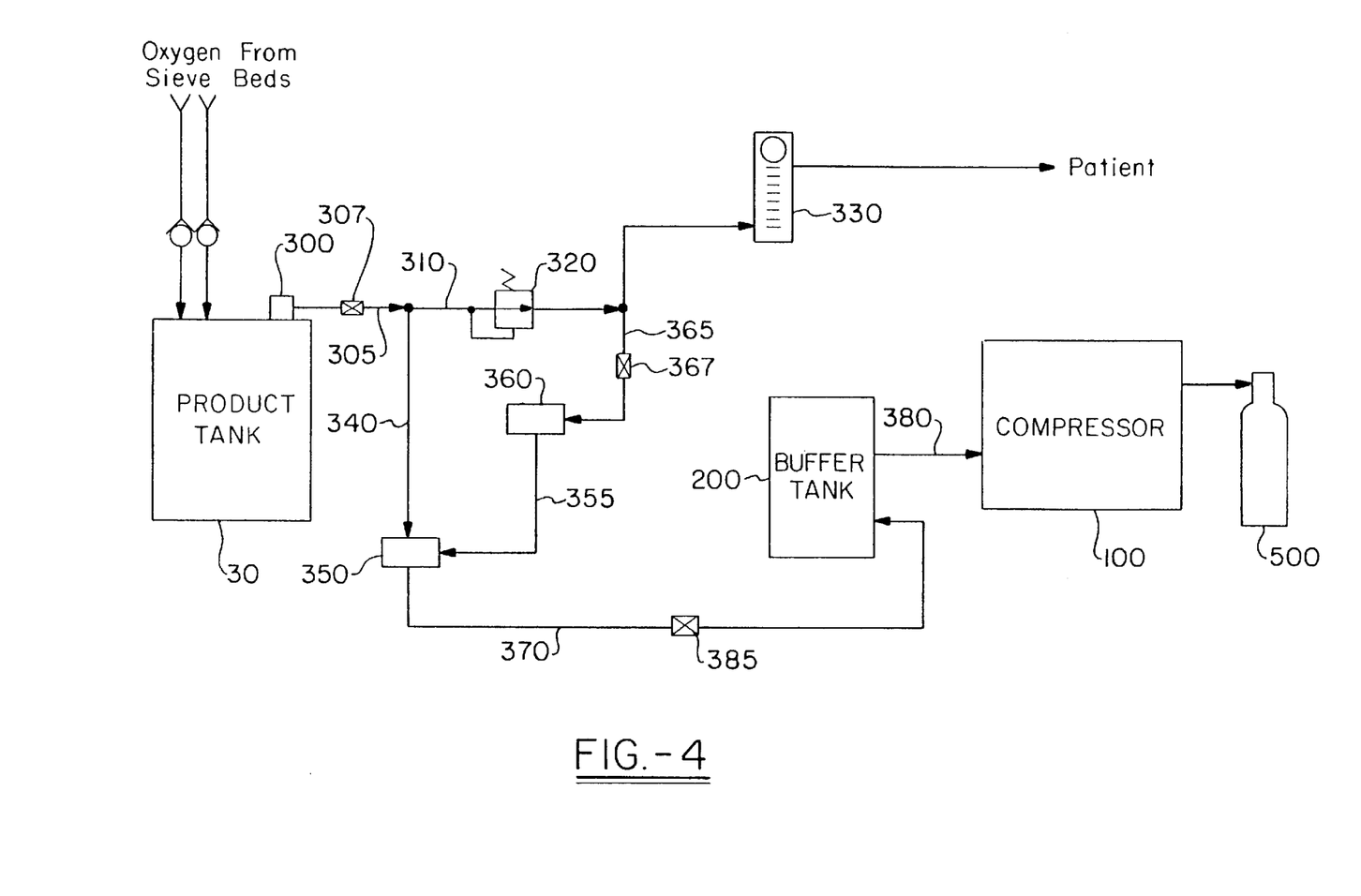
FIG. 4 is a block diagram of the apparatus and process of another embodiment of the present invention for feeding a portion of enriched gas at a controlled rate to a patient and another portion of the enriched gas to a compressor for high-pressure storage in a portable container.

FIGS. 3 and 4 relate to embodiments wherein oxygen-enriched air from product tank 30 of the oxygenator is fed by various methods desirably to a buffer tank of the compressor but prioritized as with regard to oxygen concentration and/or a sufficient pressure. For example, the feed rate to a patient can vary from between 0.1 and 6 liters per minute at a pressure of a predetermined value such as 5 psi with the remaining oxygen-enriched gas generally being fed at a different pressure to the buffer tank. The buffer tank can generally contain a broad range of pressure therein such as, for example, between 14 and 21 psi. However, as noted with regard to FIG. 2, depending upon the withdrawal rate of the gas in the buffer tank by the compressor, the pressure thereof can drop down to a predetermined cut-off pressure, such as 7 psi, which is higher than the pressure of the gas being fed to the patient to ensure an adequate flow of the oxygen-enriched gas to the patient.

Referring to the embodiment of FIG. 3, a 5-psi regulator 210 emits oxygen-enriched gas from product tank 30 into flow line 220 and feeds the same to flow meter 230 which subsequently emits the oxygen-enriched gas to the patient at a predetermined flow rate of from 0.1 to 6 liters per minute. Optionally, the flow meter can be closed so that all the enriched oxygen is directed to the compressor. Gas not directed to the patient is carried via line 240 to two-way valve 250. A very small portion of the gas in line 220 is directed through line 260 through restrictor 262 into oxygen sensor 265 which detects whether or not the concentration of the oxygen is of a predetermined value such as is at least 84 percent. When the oxygen sensor detects a concentration at or above the predetermined level, two-way valve 250 is open and permits the oxygen-enriched gas to flow through line 270 into buffer tank 200 wherein the pressure is essentially the same as the oxygen product tank pressure. However, should the oxygen sensor not detect a suitable oxygen concentration, two-way valve 250 is closed so that the oxygen concentrator can build up a sufficient oxygen concentration. This arrangement prioritizes the flow of oxygen-enriched gas so that the patient is assured of receiving a gas having a minimum oxygen concentration therein. Buffer tank 200 can have a regulator 280 thereon generally set at 12 psi to admit the oxygen-enriched gas to the compressor when needed. Alternatively, the pressure regulator can be set at anywhere from about 13 to about 21 psi. Restrictor 290 controls the flow rate of gas from the buffer tank to the compressor. Should the compressor drop the pressure in the buffer tank to below a predetermined value, a pressure sensor (not shown) will automatically cut off the flow of gas at a pressure above the pressure of the gas being fed to the patient. This prioritization assures that the patient receives priority with regard to oxygen-enriched gas.

The embodiment of FIG. 4 emits the oxygen-enriched gas through a 14 to about an 18-psi regulator 300 into flow line 305 having flow rate restrictor 307. The flow is then split with a portion via line 310 going through 5-psi regulator 320 and into flow meter 330 which then directs the gas to the patient at a desired flow rate of generally from 0.1 to 6 liters per minute, although optionally the flow meter can be closed. The remaining portion of the gas is directed via line 340 to two-way valve 350. A small portion of the gas going to the patient is diverted through line 365 through flow restrictor 367 to oxygen sensor 360. As in FIG. 3, the oxygen sensor is set at a predetermined value such as a concentration of 84 percent so that when the level is not achieved, two-way valve 350 is closed through electrical line 355. This aspect allows the amount of oxygen in the concentrator tank to be increased by the oxygenator unit. The same prioritizes the concentration of oxygen to ensure that the patient receives an amount of oxygen of at least the minimum predetermined value. When the oxygen concentration is sufficient, the gas flows through two-way valve 350 into line 370 and into buffer tank 200 where it is stored generally at a pressure of about 14 to 18 psi. A relief valve 385 which can be set at any desired value such as about 14 psi ensures that gas under sufficient pressure is being admitted to the buffer tank. The oxygen-enriched gas is admitted to the compressor via line 380. Should the compressor withdraw gas faster than it is being received by the buffer tank, the pressure therein will drop. A pressure sensor switch (not shown) can be set to a predetermined value (e.g., about 7 psi) to ensure or prioritize that a sufficient amount or flow of gas is being fed to the patient. The predetermined shut-off pressure of the compressor is always above the pressure of the gas being fed to the patient. The embodiment of FIG. 4 is preferred.

While the above description, as exemplified by FIGS. 2, 3, and 4, generally constitutes a preferred embodiment of the present invention, it is to be understood that the same can be modified. For example, oxygen product tank 30 need not be utilized. Instead, the oxygen-enriched air from an oxygen concentrator, such as shown in FIG. 1, can be fed to the buffer tank via the shown and described flow lines of the various embodiments such as set forth in FIGS. 2, 3, and 4. Accordingly, the oxygen-enriched air will be separated with one component directed to the patient and the other component being directed to the buffer tank. Prioritization of the oxygen-enriched gas to the patient either by a minimum oxygen concentration or a sufficient pressure in the buffer tank is still generally utilized. Alternatively, an enriched oxygen product tank 30 can be utilized and the buffer tank can optionally be eliminated. In other words, enriched oxygen from the product tank can be fed via one component to the patient and to a second component via the flow line shown to the compressor. In this situation, prioritization of the desired flow and oxygen concentration to the patient is maintained as described hereinabove with regard to either the level of oxygen concentration or an adequate pressure being admitted to the compressor.

Figure 7:
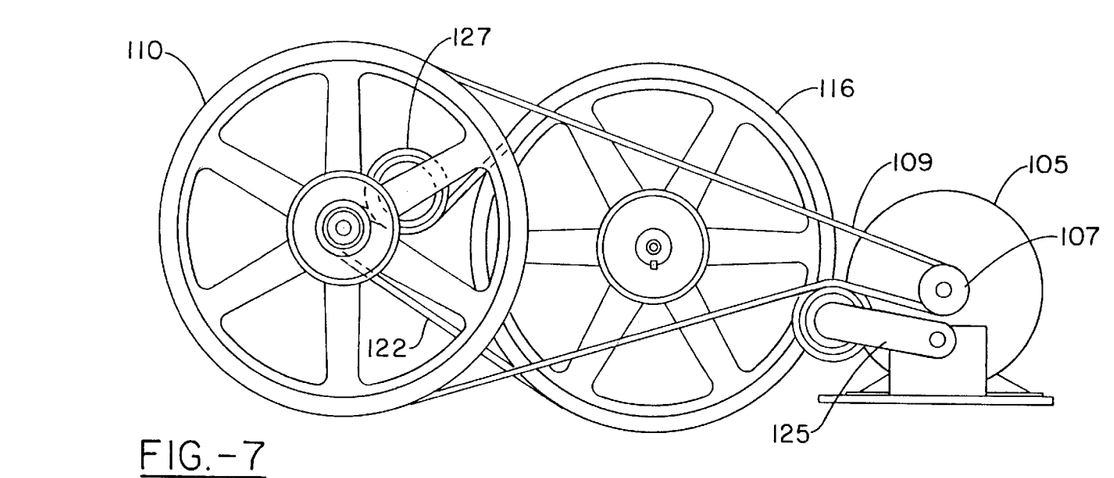
FIG. 7 is a side elevational view of the compression apparatus of the present invention.
Figure 8:
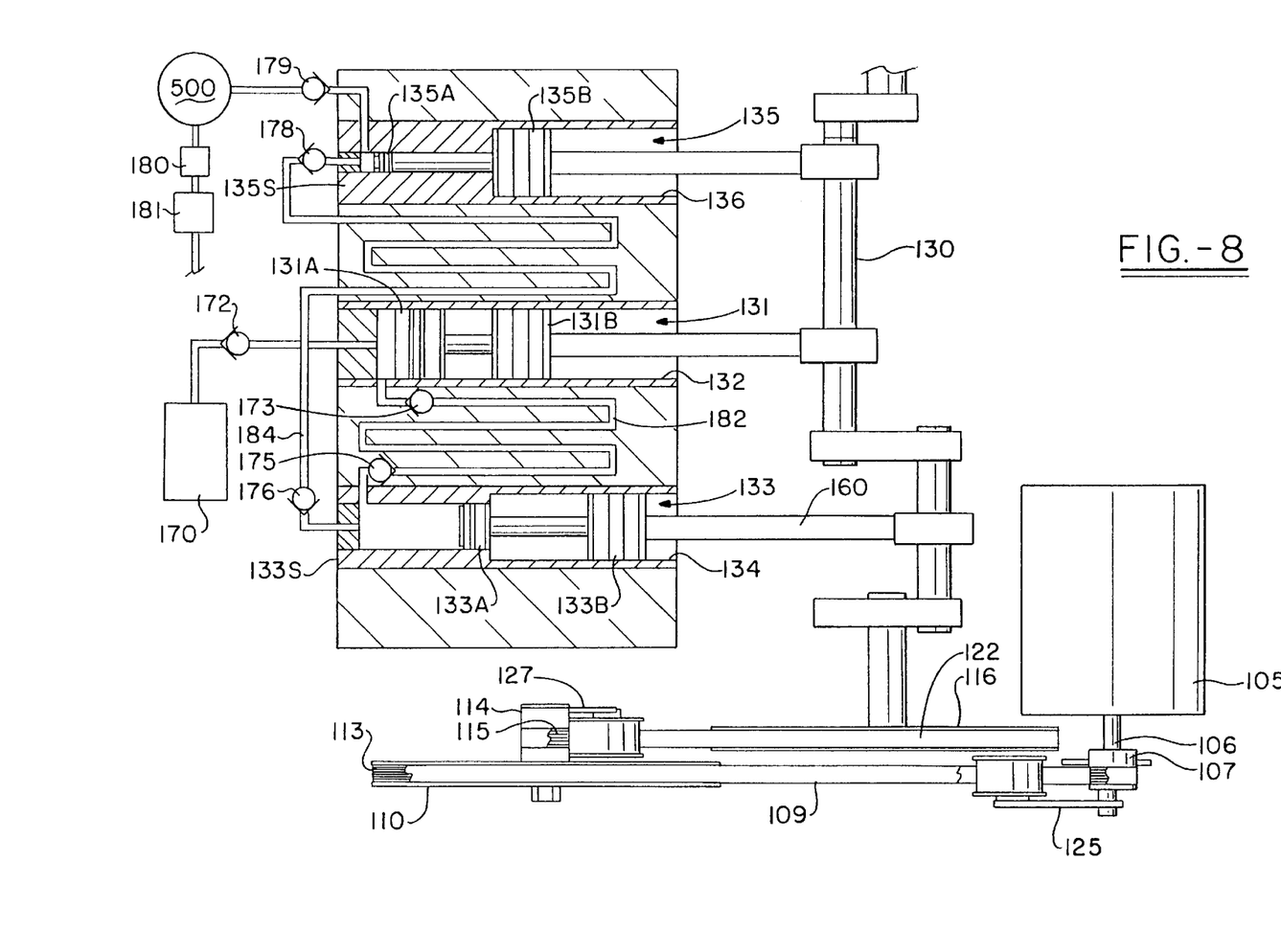
FIG. 8 is a top plan view of the compression apparatus of the present invention.

Referring now to the compressor assembly 100 as shown in FIGS. 7 and 8, it generally utilizes an AC electric-drive motor 105 which can rotate at any desired speed, e.g., 1,700 rpm. Motor 105 can contain a fan (not shown) either within the motor housing or immediately adjacent thereto to draw air through the motor to cool the same. Power is conveyed from the motor through shaft 106 to drive wheel 107. Desirably the drive wheel has a plurality of grooves therein to receive a V-belt such as main drive belt 109. Such belts are generally reinforced with fiber and have a very long life. Main drive belt 109 is connected to main gear 110 which contains a plurality of grooves 113 therein. The number of peripheral grooves 113, as well as the size and location thereof, coincides with the grooves of drive wheel 107 and matingly engage a plurality of projections located on main drive belt 109. Extending from main gear 110 is an offset hub gear 114 which has a much smaller diameter than main gear 110. Hub gear 114 also has grooves 115 thereon to receive a secondary drive V-belt 122. A second or secondary large gear 116 has grooves on the periphery thereof which matingly engage the secondary drive V-belt 122. Offset hub 114 through the secondary V-drive belt 122 contacts and serves to drive secondary gear 116 which in turn is connected to crankshaft 130.

Through the utilization of the two large gears 110 and 116, a double-reduction is obtained such that the rotational speed of crankshaft 130 is a desirably low speed such as approximately 50 rpm. Both drive belts 109 and 122 desirably have a spring-loaded idler arm 125 and 127, respectively, which applies a small amount of tension. The actual pull tension of the first belt can be about 20 pounds, whereas the tension on the second belt can be about 100 pounds.

The multi-stage compressor of the present invention can have any number of pistons, but in the present embodiment has three. As shown in FIG. 8, two of the pistons, i.e., the first and third pistons, are located on the same crankshaft lobe, whereas the second piston is located on a different lobe offset 180° from the first and third pistons. The reason for this is that pistons one and three will be drawing in air when the second piston is being compressed and vice versa. Although not shown, a crankshaft can be utilized which contains three lobes thereon, each offset from one another by approximately 110° to 130°, e.g., about 120°, so as to minimize the torque resistance applied to the motor during the compression stroke.

The compressor of the present invention has three pistons, i.e., piston #1 (131), piston #2 (133), and piston #3 (135). Each piston is contained within a separate cylinder and thus piston #1 is contained within the first cylinder (132), the second piston is contained the second cylinder (134), and the third piston is contained within the third cylinder (136).

Figure 9:
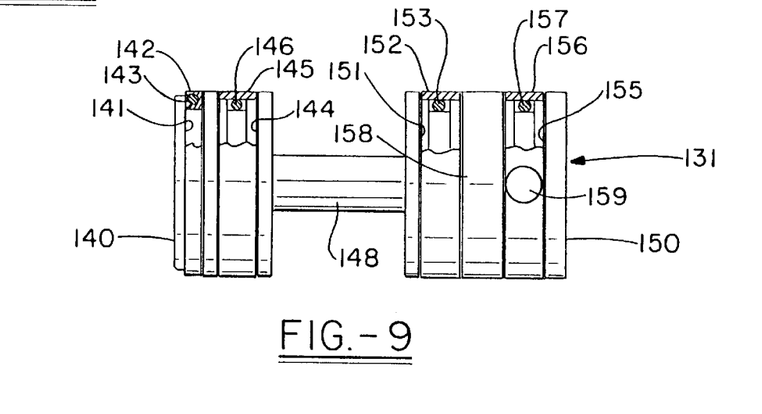
FIG. 9 is a side elevational view of the upper portion of the two-part piston assembly of the present invention.

While the diameter of the head 140 of the first piston is approximately equal to the diameter of the base portion of the piston as shown in FIGS. 8 and 9, the diameter of the head of piston #2 (133) is smaller than that of piston #1, and the diameter of the head of piston #3 (135) is smaller than the diameter of piston #2 (133). However, the base of each piston 131B, 133B, and 135B is of the same size for reasons set forth hereinbelow. In order to permit pistons #2 and #3-to operate properly, each contains an annular sleeve 134S and 136S on the inside of the cylinder wall the internal diameter of which is approximately equal to the external diameter of piston heads #2 and #3 respectively.

Regardless of the size of the piston head, it has two rings as generally indicated in FIG. 9. Inasmuch as the rings of all three piston heads are generally the same, only the first piston is shown in FIG. 9. The piston head has two annular grooves or recesses therein, that is top piston annulus 141 and bottom annulus 144. The top annulus contains a U-shaped seal therein generally made out of a Teflon® alloy or other low-friction material. The seal contains a coil tension spring 143 therein which forces the seal radially outward against the cylinder wall to prevent compressed air from leaking through the piston head between the piston and the cylinder wall. To also ensure the maintenance of a good seal, seal 142 is U-shaped so that upon the build-up of pressure in the cylinder head, the compressed gas will communicate and enter into the seal and force the outer edge thereof radially outward against the cylinder wall. Piston head bottom annulus 144 contains a flat or vertical glide ring 145 which extends around the annulus and is also radially forced outwardly by a coil tension spring 146 located therein. The bottom glide ring 145 can be made out of a Teflon® alloy and serves as a piston glide ring.

Connecting rod 148 connects the piston head to piston base 150. The piston bases of all three pistons are the same diameter and accordingly engage a mating cylinder of essentially the same diameter. The piston base contains an upper base annulus 151 and a lower base annulus 155, both of which have a glide ring therein similar to if not identical to glide ring 145 of piston head annulus 144. Thus, upper base annulus 151 has a glide ring 152 therein which is forced radially outward by coil spring 153. Similarly, lower base annulus 155 has a glide ring 156 therein which is radially forced out by coil spring 157. Although three glide rings have been shown and described as being identical, they can be different and use different material, and the like. Piston base 150 contains bore 158 which extends laterally therethrough. Bore 158 receives wrist pin 159. The wrist pin and coil spring both serve to maintain glide ring 156 in a radially outward position so as to bear against the cylinder wall.

Figure 10:
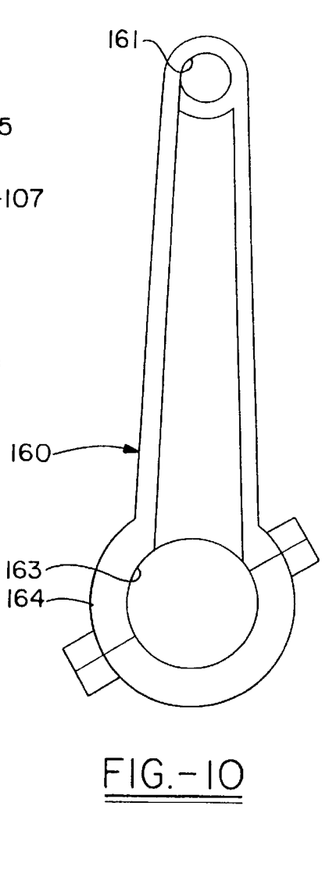
FIG. 10 is a side elevational view of the bottom portion of the two-part piston assembly of the present invention.

The two-part piston assembly of the present invention contains bottom connecting rod 160 as shown in FIG. 10. The connecting rod contains a top bore 161 through which wrist pin 159 extends. Bottom bore 163 of the connecting rod extends about and matingly engages an appropriate portion of the crankshaft. In order to permit rotation of connecting rod 160 about the crankshaft 130, sealed portion 164 of the connecting rod contains bearings therein.

The net result of the two-part piston ring assembly of the present invention is that bearing 164 of connecting rod 160 can freely rotate with the crankshaft in a rotary or circular motion whereas top bore 161 moves in only a linear or reciprocal motion allowing piston rod 148 with the piston head and base thereon to move only in a linear reciprocating direction. The same thus prevents lateral forces from being applied to the cylinder wall which often results in wear and can create an oval-shaped cylinder wall. The two piston ring assembly of the present invention thus promotes long life of the piston and cylinder wall.

Although each piston serves to compress the gas admitted therein to a higher pressure, a desirable aspect of the present invention, as noted above, is that each subsequent piston head has a smaller area. For example, piston #1 (131) can have a diameter of approximately 1¾ inches, whereas piston #2 has a diameter of approximately ¼ inches, and piston #3 can have a diameter of approximately ½ inch, which can be the diameter of essentially piston rod 148. Desirably, the increase in pressure from each stage or piston is proportional to the others. The compression ratio of each piston can vary, but generally is the same. Although compression ratios of up to 10 can be utilized, the desirable pressure range is from approximately 6 to about 8.

Inasmuch as heat is built-up during compression of the oxygen-enriched gas, the flow lines between the pistons can be extended so that they are long enough to permit the heat of compression to be absorbed by ambient air and thus cool the enriched pressurized gas therein. As shown in FIG. 8, cooling line 182 from the first piston to the second piston can be in the form of an undulating path or the like and the same is true with regard to cooling line 184 between the second and third pistons.

The operation of the compressor portion of the apparatus is as follows. Electric motor 105 which operates independently of the compressor feeding air to the molecular sieves in the oxygen concentrator portion of the apparatus, through drive belts 109 and 122, rotates crankshaft 130 thereby causing piston #1, #2, and #3 (131, 133, 135) to reciprocate and compress air in their respective chambers. More specifically, enriched oxygen gas from the compressor buffer tank is fed to the first piston. Piston 131 contains an inlet check valve 172, which permits air to enter the cylinder head space above the piston, and outlet check valve 173, which permits the compressed gas to exit from the first piston. The check valves permit flow of the gas in one direction so that once the gas is admitted to the first piston, during the compression stroke thereof it cannot be forced back out to the buffer tank. Similarly, once forced out of the first piston, outlet check valve 173 prevents the gas from being sucked in during the intake stroke of the first piston. In a similar manner, second piston 133 has an inlet check valve 175 which permits the compressed air from piston #1 to be drawn into the head space above piston 133, but prevents it from being forced back into the first piston. Outlet check valve 176 prevents the gas compressing the second piston from being drawn back into the piston once it has been expelled therefrom. In a similar manner, the gas which has been further compressed in piston #2 is fed into piston #3 (135) through inlet check valve 178 where it is further compressed. The compressed gas is then fed through outlet check valve 179 into enriched oxygen gas storage cylinder 500. Outlet check valve 179 thus prevents the highly stored gas in the cylinder from being admitted back into the third piston.

During the operation of the compressor, the gas in portable cylinder 500 which is initially at ambient pressure, is gradually built up to desired pressure. One such suitable pressure is approximately 2,250 psi. Of course, different cylinders can accept either higher or lower gas pressures and readily maintain the same. Rupture disk 180 is a safety feature designed to rupture at a pressure in excess of the desired storage pressure of the gas cylinder. Thus, in the present embodiment, such a pressure can be approximately 2,800 psi. Although not shown, rupture disks can also be provided in the flow lines from the exit of the first and second cylinders to prevent undue build-up in these lines. A pressure regulator 181 serves to emit the oxygen-enriched gas at a pressure of about 5 psi to a patient via a flow meter (not shown) at any desired rate, such as from about 0.1 to about 6 liters per minute.

As previously noted, the buffer tank contains oxygen-enriched gas at a pressure of generally from about 7 or 14 psi to about 21 psi. The compressor is designed to commence compression generally when the pressure in the tank is generally at a maximum until it drops to a predetermined pressure, e.g., 7 or 8 psi. In general, the pressure is electrically controlled by various switches, sensors, relays and the like. Briefly, a master ON/OFF switch emits power to compressor motor 105 which in turn causes the crankshaft to rotate and compress air. Two pressure-sensitive switches exist: a low pressure sensor which detects pressure below a predetermined value, e.g., 7 to 12 psi, and a high pressure sensor which detects pressure above 2,250 psi. When the low pressure sensor detects pressure below the predetermined level, it will turn off motor 105 through a relay switch. This allows oxygen inflow from the concentrator to be built-up in the buffer tank to a desired pressure. The low pressure sensor is a solid-state relay. Should the relay fail, it will fail closed and allow the motor to continue to run. Accordingly, this relay switch is connected in series with the high pressure sensor mechanical relay switch which will shut the motor off when the pressure in the cylinder reaches approximately 2,250 psi.

Figure 5:
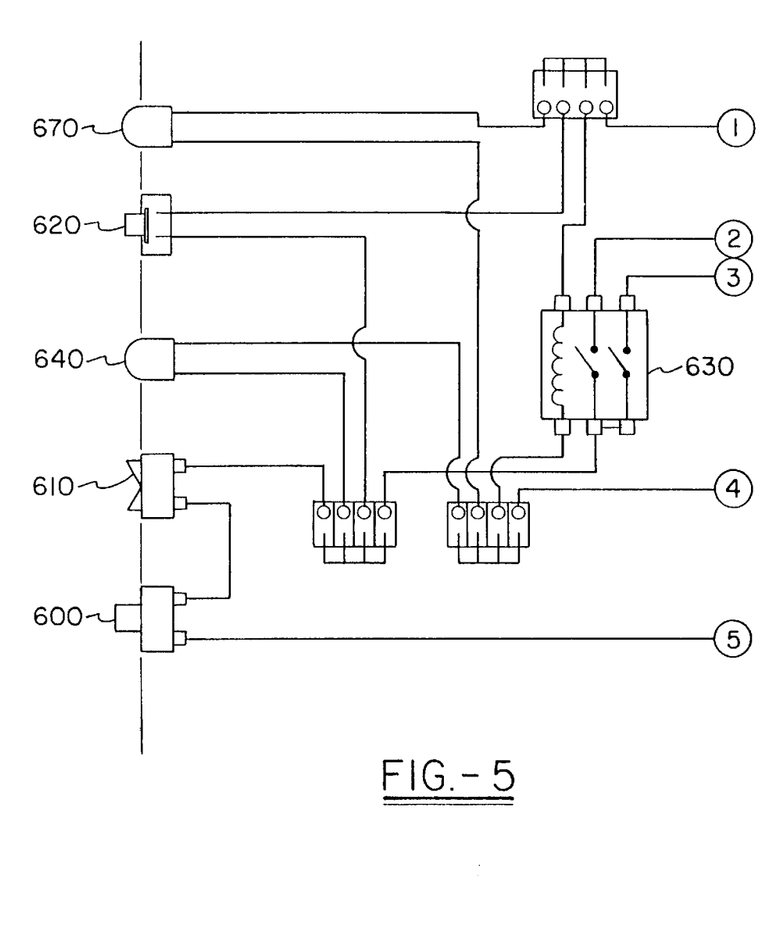
FIG. 5 is a schematic showing one portion of a control circuit for operating a multiple-stage compressor of the present invention.
Figure 6:
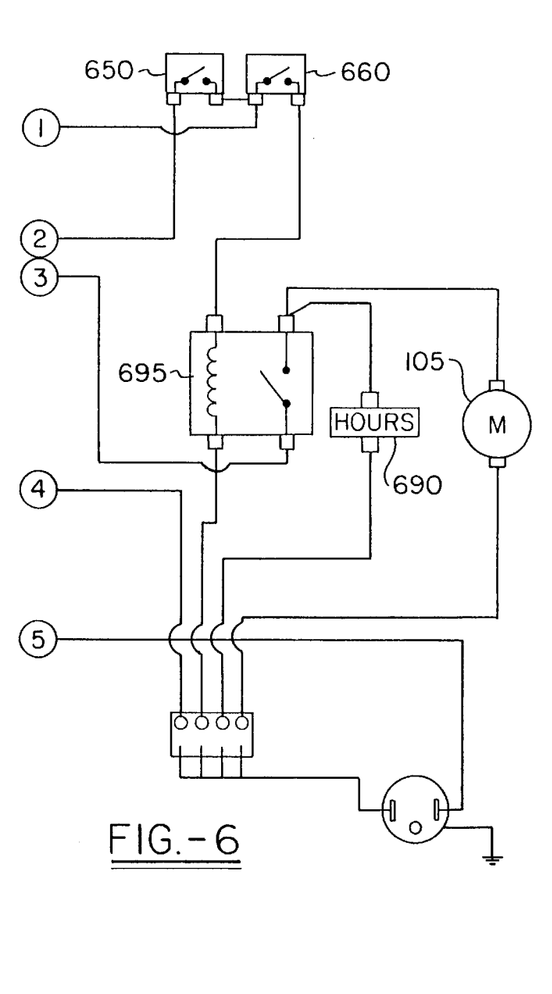
FIG. 6 is a schematic of the remaining portion of the control circuit of FIG. 5 for operating a multiple-stage compressor of the present invention.

FIGS. 5 and 6 show the electrical circuitry of the compressor. Power is fed to the compressor initially through the resettable breaker 600 and then to power switch 610. When the power switch is pushed to the "ON" position, power passes to the motor start switch 620, the start relay common contacts 630, and also lights the power indicator 640. When start switch is depressed, the start relay coil is energized which causes both switches of the relay to close.

One of these closed switches passes the power to high pressure switch 650 which is normally closed when the output pressure of the compressor is under 2,250 psi. The output of the high pressure switch is fed back to the start relay coil to keep the coil energized without the start switch being depressed, but will cut power to the coil when high pressure is reached. (This occurs when a tank has been filled.) The output of the high pressure switch is also connected to the common of low pressure switch 660. While the input pressure from the concentrator is above the predetermined value, e.g., 7 psi, the low pressure switch is closed and the normally closed contact has power. This power signal is fed to the drive contact of the solid-state relay which, in turn, allows the solid-state output to be "turned on." The output of the high-pressure switch is also connected to the run indicator 670 which then lights up.

The second closed switch of the start relay is connected to the "input" of the solid-state relay. When the solid-state relay is turned on by the signal from the low pressure switch, power is passed to motor 105 and its start capacitors through the solid-state output. A common line is connected to the other side of the motor to complete the circuit. An hour meter 690 is wired in parallel to the motor to monitor motor run time.

When the above occurs, the motor beings to run and remains running until one of two conditions occur. The first condition would be the input pressure to the compressor falls below a predetermined value, e.g., 7 psi. This will cause low pressure switch 660 to open and solid-state relay 695 to turn off, which in turn shuts off motor 105. If the input pressure to the compressor rises above a desired predetermined pressure, low pressure switch 660 will close and once again turn on the solid-state relay and start the motor. This is a normal occurrence that is dependent upon concentrator efficiency and may be repetitive.

The second condition that will shut off the motor occurs when an oxygen tank has been filled. The output pressure will rise above 2,250 psi and therefore cause high pressure switch 650 to open. This cuts the power to the start relay coil which causes both switches to open and cuts the power to both the input of the high pressure switch and the input to the solid-state relay thereby shutting off the motor. To start the motor after this condition is reached requires start switch 620 to be depressed. If greater than 2,250 psi remains, the high pressure switch will remain open and no signal will be fed back to the start relay coil to keep it energized therefore causing the motor to remain off. While the high pressure switch is open, run indicator 670 remains off.

Any direct shorts between power and common or any condition that draws more than 8 amps of current will cause resettable breaker 600 to pop open.

As apparent from the above, the operation of compressor 100 is completely independent of the oxygen concentrator and utilization of gas compressed thereby as a power or energy source. In other words, the pressure accumulated in the oxygen concentrator is not utilized to drive or operate any pistons in the compression portion 100 of the apparatus.

A distinct advantage of the apparatus and method for forming oxygen-enriched gas and compression thereof according to the present invention is the creation of a mobile or portable source of gas containing high purity oxygen. Patients who require oxygen-enriched gas, as from about 80 to about 98 percent, are no longer confined to the vicinity of an oxygen concentrator as for example a bed, home, hospital, or a wheelchair. Rather, the patient can carry the mobile gas cylinder in any convenient manner, such as in a backpack, and thus can take trips via wheelchair, an automobile, and even planes and trains. Depending upon the pressure and size of the storage cylinder, the oxygen supply can be anywhere from about 2 to about 24 hours or even longer.

While in accordance with the patent statutes the best mode and preferred embodiment has been set forth, the scope of the invention is not limited thereto, but rather by the scope of the attached claims.

What is claimed is:

1. An apparatus for compressing and storing an oxygen-enriched gas, comprising;
   an oxygen concentrator product tank having oxygen-enriched gas therein, wherein said oxygen-enriched gas contains at least about 70% oxygen by volume; a piston compressor operatively connected to said oxygen concentrator product tank to receive prioritized oxygen-enriched gas therefrom;
   said compressor operated by a power source other than oxygen-enriched gas from said concentrator product tank and being capable of compressing said oxygen-enriched gas to a high pressure; and
   a high-pressure storage container for portable storage of said high-pressure oxygen-enriched gas.

2. An apparatus according to claim 1, wherein said oxygen-enriched gas is prioritized by primarily being capable of being fed to a person and secondarily any excess oxygen-enriched gas being capable of being fed to said compressor, said prioritization including a determination of the oxygen concentration of said gas by an oxygen sensor and the termination of said oxygen-enriched gas being fed to said compressor when said oxygen level is below a predetermined oxygen concentration.

3. An apparatus according to claim 1, wherein said oxygen-enriched gas is prioritized by primarily being capable of being fed to a person and any excess oxygen-enriched gas being capable of being fed to said compressor, wherein said prioritization includes a low pressure sensor which is capable of cutting off the flow of said oxygen-enriched gas to said compressor when the pressure to said compressor is below a predetermined level which is greater than the pressure of the oxygen-enriched gas being fed to a patient.

4. An apparatus according to claim 1, including a buffer tank, said buffer tank operatively connected to said oxygen concentrator product tank and to said compressor, wherein said oxygen-enriched gas is prioritized by primarily being capable of being fed to a person and secondarily any excess oxygen-enriched gas being capable of being fed to said buffer tank, said prioritization including a determination of the oxygen concentration of said gas by an oxygen sensor and the termination of said oxygen-enriched gas being fed to said buffer tank when said oxygen level is below a predetermined oxygen concentration.

5. An apparatus according to claim 1, including a buffer tank, said buffer tank operatively connected to said oxygen concentrator product tank and to said compressor, and wherein said oxygen-enriched gas is prioritized by primarily being capable of being fed to a person and any excess oxygen-enriched gas being capable of being fed to said buffer tank, wherein said prioritization includes a low pressure sensor which is capable of cutting off the flow of said oxygen-enriched gas to said buffer tank when the pressure to said buffer tank is below a predetermined level which is greater than the pressure of the oxygen-enriched gas being fed to a patient.

6. An apparatus according to claim 4, wherein said oxygen-enriched gas is compressed by a multi-stage compressor, wherein said multi-stage compressor contains a plurality of cylinders each having a piston therein, wherein said oxygen-enriched gas is sequentially compressed by each piston, and wherein each sequential piston has a smaller diameter than the prior piston.

7. An apparatus according to claim 5, wherein said oxygen-enriched gas is compressed by a multi-stage compressor, wherein said multi-stage compressor contains a plurality of cylinders each having a piston therein, wherein said oxygen-enriched gas is sequentially compressed by each piston, and wherein each sequential piston has a smaller diameter than the prior piston.

8. An apparatus according to claim 6, wherein each said piston has a head portion and a separated base portion, wherein said head portion and base portion reciprocate within said cylinder, and wherein said head portion and said base portion are connected by a piston rod.

9. An apparatus according to claim 7, wherein each said piston has a head portion and a separated base portion, wherein said head portion and base portion reciprocate within said cylinder, and wherein said head portion and said base portion are connected by a piston rod.

10. A process for filling a portable container having an oxygen-enriched gas under high pressure, comprising the steps of;
enriching atmospheric air in an oxygen concentrator to a concentration of at least about 50 percent oxygen;
transferring said oxygen-enriched gas to a piston compressor at an initial pressure level;
compressing said oxygen-enriched gas admitted to said compressor to a high-pressure; and
transferring said high-pressure, oxygen enriched gas to a portable container for subsequent use by a patient.

11. A process according to claim 10, including prioritizing said oxygen-enriched gas by feeding a portion thereof at a minimum oxygen concentration to a patient.

12. A process according to claim 10, including a buffer tank, transferring said oxygen-enriched gas to said buffer tank, transferring said oxygen-enriched gas from said buffer tank to said compressor, apportioning said oxygen-enriched gas to a patient, and prioritizing said apportioned oxygen-enriched gas to a patient upon the basis of terminating the flow of said oxygen-enriched gas to said buffer tank when the pressure in said buffer tank is below a predetermined level which is greater than the pressure of the oxygen-enriched gas being fed to a patient.

13. A process according to claim 12, including a buffer tank, transferring said oxygen-enriched gas to said buffer tank, transferring said oxygen-enriched gas from said buffer tank to said compressor, apportioning said oxygen-enriched gas to a patient, and prioritizing said apportioned oxygen-enriched gas to a patient upon the basis of determining the oxygen concentration of said gas and terminating said oxygen-enriched gas being fed to said buffer tank when said oxygen level is below a predetermined oxygen concentration.

14. A process according to claim 10, including compressing said oxygen-enriched gas in a multi-stage compressor.

15. A process according to claim 12, including compressing said oxygen-enriched gas in a multi-stage compressor, and sequentially compressing said gas in said compressor wherein each subsequent stage has a smaller piston compression area.

16. A process according to claim 15, wherein said portable container contains said oxygen-enriched gas at a pressure of at least about 2,500 psi and at a concentration of at least 80 percent oxygen.

17. An apparatus for collecting and storing or distributing an oxygen-enriched gas, comprising;
a first compressor for providing a source of low pressure air;
a first storage vessel having an inlet and an outlet;
an oxygen concentration device having an inlet which receives said low pressure air from said source and an outlet which provides a source of oxygen-enriched gas at a relatively low pressure to said first storage vessel inlet;
a pressure control device which receives a first component of said low pressure oxygen-enriched gas and outputs said oxygen-enriched gas at a reduced set pressure for use by a patient;
a buffer tank having an outlet and an inlet adapted to receive a second component of said oxygen-enriched gas at said low pressure from said first storage tank outlet;
a second storage vessel having an inlet and an outlet;
a second compressor connected to said buffer tank outlet which further compresses said oxygen-enriched gas and outputs oxygen-enriched gas at a relatively high pressure to said inlet of said second storage vessel;
prioritizing apparatus connected between the outlet of said first storage vessel and said second compressor and which interrupts the flow of said second component of oxygen-enriched gas to said second compressor when the pressure of said second component of oxygen-enriched gas falls below a preset amount to ensure that said first component is sufficient to ensure the output of said pressure control device is at said reduced set pressure.

18. The apparatus of claim 17, comprising:
a valve element connected between the outlet of said first storage vessel and said second compressor; and
an oxygen concentration detector operatively connected to said valve element which monitors said first component of said low pressure oxygen-enriched gas and which operates said valve element to interrupt the flow of said second component of oxygen-enriched gas to said second compressor when the concentration of said second component of oxygen-enriched gas reaches a set limit.

19. An apparatus for collecting and storing or distributing an oxygen-enriched gas, comprising;
a first compressor for providing a source of low pressure air;
a first storage vessel having an inlet and an outlet;
an oxygen concentration device having an inlet which receives said low pressure air from said source and an outlet which provides a source of oxygen-enriched gas at a relatively low pressure to said first storage vessel inlet;
a pressure control device which receives a first component of said low pressure oxygen-enriched gas and outputs said oxygen-enriched gas at a reduced set pressure for use by a patient;
a buffer tank having an outlet and an inlet adapted to receive a second component of said oxygen-enriched gas at said low pressure from said first storage tank outlet;
a second storage vessel having an inlet and an outlet;
a second compressor connected to said buffer tank outlet which further compresses said oxygen-enriched gas and outputs oxygen-enriched gas at a relatively high pressure to said inlet of said second storage vessel;
a valve element connected between the outlet of said first storage vessel and said second compressor; and
an oxygen concentration detector operatively connected to said valve element which monitors said first component of said low pressure oxygen-enriched gas and which operates said valve element to interrupt the flow of said second component of oxygen-enriched gas to said second compressor when the concentration of said second component of oxygen-enriched gas reaches a set low limit.

20. An apparatus for compressing and storing an oxygen-enriched gas, comprising;
an oxygen concentrator to produce enriched oxygen, a buffer tank operatively connected to said oxygen concentrator to receive prioritized oxygen-enriched gas therefrom;
a compressor operatively connected to said buffer tank to receive said oxygen-enriched gas, said compressor operated by a power source other than oxygen-enriched gas from said oxygen concentrator and being capable of compressing said oxygen-enriched gas to a high pressure, and
a high-pressure storage container for portable storage of said high-pressure oxygen-enriched gas.

21. An apparatus according to claim 20, wherein said oxygen-enriched gas is prioritized by primarily being capable of being fed to a person and secondarily any excess oxygen-enriched gas being capable of being fed to said buffer tank, said prioritization including a determination of the oxygen concentration of said gas by an oxygen sensor and the termination of said oxygen-enriched gas being fed to said buffer tank when said oxygen level is below a predetermined oxygen concentration.

22. An apparatus according to claim 20, wherein said oxygen-enriched gas is prioritized by primarily being capable of being fed to a person and any excess oxygen-enriched gas being capable of being fed to said buffer tank, wherein said prioritization includes a low pressure sensor which is capable of cutting off the flow of said oxygen-enriched gas to said buffer tank when the pressure to said buffer tank is below a predetermined level which is greater than the pressure of the oxygen-enriched gas being fed to a patient.

23. An apparatus according to claim 21, wherein said compressor has a plurality of compressing stages therein, and including an oxygen concentrator product tank having enriched oxygen therein, said oxygen concentrator product tank operatively connected to said oxygen concentrator and to said buffer tank.

24. An apparatus according to claim 22, wherein said compressor has a plurality of compressing stages therein, and including an oxygen concentrator product tank having enriched oxygen therein, said oxygen concentrator product tank operatively connected to said oxygen concentrator and to said buffer tank.

25. An apparatus for collecting and storing or distributing an oxygen-enriched gas, comprising;
a first compressor for providing a source of low pressure air;
an oxygen concentration device having an inlet which receives said low pressure air from said source and an outlet which provides a source of oxygen-enriched gas at a relatively low pressure to a buffer tank;
a pressure control device which receives a first component of said low pressure oxygen-enriched gas and outputs said oxygen-enriched gas at a reduced set pressure for use by a patient;
said buffer tank having an outlet and an inlet adapted to receive a second component of said oxygen-enriched gas at said low pressure from said oxygen concentration device;
a second storage vessel having an inlet and an outlet;
a second compressor connected to said buffer tank outlet which further compresses said oxygen-enriched gas and outputs oxygen-enriched gas at a relatively high pressure to said inlet of said second storage vessel;
prioritizing apparatus connected between said oxygen concentrator and said second compressor and which interrupts the flow of said second component of oxygen-enriched gas to said second compressor when the pressure of said second component of oxygen-enriched gas falls below a preset amount to ensure that said first component is sufficient to ensure the output of said pressure control device is at said reduced set pressure.

26. An apparatus for collecting and storing or distributing an oxygen-enriched gas, comprising;
a first compressor for providing a source of low pressure air;
an oxygen concentration device having an inlet which receives said low pressure air from said source and an outlet which provides a source of oxygen-enriched gas at a relatively low pressure to a buffer tank;

a pressure control device which receives a first component of said low pressure oxygen-enriched gas and outputs said oxygen-enriched gas at a reduced set pressure for use by a patient;

said buffer tank having an outlet and an inlet adapted to receive a second component of said oxygen-enriched gas at said low pressure from said oxygen concentration device;

a second storage vessel having an inlet and an outlet;

a second compressor connected to said buffer tank outlet which further compresses said oxygen-enriched gas and outputs oxygen-enriched gas at a relatively high pressure to said inlet of said second storage vessel;

a valve element connected between said oxygen concentration device and said second compressor; and an oxygen concentration detector operatively connected to said valve element which monitors said first component of said low pressure oxygen-enriched gas and which operates said valve element to interrupt the flow of said second component of oxygen-enriched gas to said second compressor when the concentration of said second component of oxygen-enriched gas reaches a set low limit.

* * * * * the

(12) EX PARTE REEXAMINATION CERTIFICATE (6414th)
United States Patent
Richey, II et al.

(10) Number: US 5,988,165 C1
(45) Certificate Issued: Sep. 2, 2008

(54) APPARATUS AND METHOD FOR FORMING OXYGEN-ENRICHED GAS AND COMPRESSION THEREOF FOR HIGH-PRESSURE MOBILE STORAGE UTILIZATION

(75) Inventors: Joseph B. Richey, II, Chagrin Falls, OH (US); Gerold G. Goertzen, Brunswick, OH (US)

(73) Assignee: Invacare Corporation, Elyria, OH (US)

Reexamination Request:
No. 90/008,167, Aug. 16, 2006

Reexamination Certificate for:
Patent No.: 5,988,165
Issued: Nov. 23, 1999
Appl. No.: 08/942,063
Filed: Oct. 1, 1997

(51) Int. Cl.
*A62B 7/10* (2006.01)
*A62B 19/00* (2006.01)
*A62B 23/02* (2006.01)

(52) U.S. Cl. ............... 128/205.12; 128/205.11; 128/205.27; 128/204.22

(58) Field of Classification Search ............... 128/204.22
See application file for complete search history.

(56) References Cited

U.S. PATENT DOCUMENTS

| | | | |
|---|---|---|---|
| 4,428,372 A | * | 1/1984 | Beysel et al. ............ 128/202.26 |
| 4,860,803 A | | 8/1989 | Wells |
| 5,405,249 A | | 4/1995 | Benson |
| 5,858,062 A | | 1/1999 | McCulloh et al. |
| 5,893,275 A | | 4/1999 | Henry |
| 5,988,165 A | | 11/1999 | Richey, II |

OTHER PUBLICATIONS

RIX Industries, "RIX SA Air Compressors—Oil–Free Breathing Air To 4,500 PSIG", 2 pages, undated.

* cited by examiner

*Primary Examiner*—Aaron J. Lewis (57) ABSTRACT

An oxygen concentrator is utilized in combination with a compressor to provide a highly enriched and compressed oxygen gas in a mobile container such as a gas cylinder. The combination and method of production provides for the facile preparation of an enriched source of oxygen for use by an ambulatory or wheelchair-confined patient. The oxygen concentrator utilizes two or more molecular sieves to provide a breathable gas of from approximately 80 to about 98 percent oxygen from atmospheric air. The oxygen-enriched gas is stored in a concentrator product tank and can be prioritized so as to supply a patient with a proper amount and concentration of oxygen and secondarily to supply any surplus or excess enriched oxygen to a compressor. The compressor utilizes multiple stages to produce the highly compressed oxygen-enriched gas and utilizes a two-part piston at low rpm to enhance low wear and low noise.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claim 1 is confirmed.

Claims 10 and 13 are determined to be patentable as amended.

New claims 27–30 are added and determined to be patentable.

Claims 2–9, 11, 12 and 14–26 were not reexamined.

10. A process for filling a portable container having an oxygen-enriched gas under high pressure, comprising the steps of:
   enriching atmospheric air in an oxygen concentrator to a concentration of at least about 50 percent oxygen;
   *transferring said oxygen-enriched gas to a tank operatively connected to a piston compressor, wherein said tank comprises an oxygen concentrator product tank or a buffer tank;*
   *prioritizing said oxygen-enriched gas between a patient output and said piston compressor;*
   transferring said oxygen-enriched gas to [a] *said* piston compressor at an intial pressure level;
   compressing said oxygen-enriched gas admitted to said compressor to a high-pressure; and
   transferring said high-pressure, oxygen enriched gas to a portable container for subsequent use by a patient.

13. A process according to claim [12] *10*, including a buffer tank, transferring said oxygen-enriched gas to said buffer tank, transferring said oxygen-enriched gas from said buffer tank to said compressor, apportioning said oxygen-enriched gas to a patient, and prioritizing said apportioned oxygen-enriched gas to a patient upon the basis of determining the oxygen concentration of said gas and terminating said oxygen-enriched gas being fed to said buffer tank when said oxygen level is below a predetermined oxygen concentration.

*27. A process for filling a portable container having an oxygen-enriched gas under high pressure, comprising the steps of:*
   *enriching atmospheric air in an oxygen concentrator to a concentration of at least about 50 percent oxygen;*
   *transferring said oxygen-enriched gas to a tank operatively connected to a piston compressor, wherein said tank comprises an oxygen concentrator product tank or a buffer tank;*
   *prioritizing said oxygen-enriched gas between a patient output and said piston compressor;*
   *transferring said oxygen-enriched gas to said piston compressor at an initial pressure level;*
   *compressing said oxygen-enriched gas admitted to said compressor to a high-pressure; and*
   *transferring said high-pressure, oxygen enriched gas to a portable container.*

*28. The process of claim 27 wherein prioritizing said oxygen-enriched gas comprises monitoring a pressure of said oxygen-enriched gas.*

*29. A process for filling a portable container having an oxygen-enriched gas under high pressure, comprising the steps of:*
   *enriching atmospheric air in an oxygen concentrator to a concentration of at least about 50 percent oxygen;*
   *transferring said oxygen-enriched gas to a tank operatively connected to a piston compressor, wherein said tank comprises an oxygen concentrator product tank or a buffer tank;*
   *feeding a quantity of oxygen-enriched gas to a patient output;*
   *monitoring said quantity of said oxygen-enriched gas being fed to said patient output;*
   *transferring said oxygen-enriched gas to said piston compressor at an initial pressure level for so long as the monitored quantity of oxygen-enriched gas is above a threshold value;*
   *compressing said oxygen-enriched gas admitted to said compressor to a high-pressure; and*
   *transferring said high-pressure, oxygen enriched gas to a portable container for subsequent use by a patient.*

*30. The process of claim 29 wherein monitoring said oxygen-enriched gas comprises monitoring a pressure of said oxygen-enriched gas.*

* * * * *